United States Patent [19]

Muoio

[11] Patent Number: 4,726,519

[45] Date of Patent: Feb. 23, 1988

[54] INSTANT/CONTINUOUS AIR-TREATMENT DEVICE

[75] Inventor: Erland L. Muoio, Racine, Wis.

[73] Assignee: S. C. Johnson & Son, Inc., Racine, Wis.

[21] Appl. No.: 823,903

[22] Filed: Jan. 27, 1986

[51] Int. Cl.[4] .................. A24F 25/00; B05B 9/00; B65D 88/54; B65D 83/00

[52] U.S. Cl. .................... 239/49; 239/51.5; 239/55; 239/57; 239/289; 239/326; 222/402.13; 222/331

[58] Field of Search ............ 239/44, 49, 51.5, 55, 239/57, 289, 326, 436, 556, 562; 222/187, 331, 402.13

[56] References Cited

U.S. PATENT DOCUMENTS

| | | | |
|---|---|---|---|
| 2,520,368 | 8/1950 | Landau | 239/47 |
| 2,987,261 | 6/1961 | McCuiston et al. | 239/304 |
| 3,017,117 | 1/1962 | Klingler | 239/57 X |
| 3,134,544 | 5/1964 | Copley | 239/55 |
| 3,185,349 | 5/1965 | Sagarin | 222/402.13 X |
| 3,330,481 | 7/1967 | Dearling | 239/47 |
| 3,940,024 | 2/1976 | Russo et al. | 222/182 |
| 3,972,473 | 8/1976 | Harrison | 239/34 |
| 4,084,732 | 4/1978 | Dearling | 222/402.17 |
| 4,235,373 | 11/1980 | Clark | 239/34 |
| 4,327,056 | 4/1982 | Gaiser | 422/124 |
| 4,341,348 | 7/1982 | Dearling | 239/34 |

Primary Examiner—Andres Kashnikow
Assistant Examiner—Patrick N. Burkhart

[57] ABSTRACT

A device for both instant and continuous dispensing of an air-treating composition. The device has a pressurized vessel with a valve stem, an actuator-overcap, and an absorbent member adjacent to vented actuator-overcap walls. The actuator-overcap, which is preferably a single integrally-molded piece, has an actuator button and a channel member engaged with the stem and terminating in a spray orifice. The channel member and/or the valve stem have outlets for directing liquid onto the absorbent member, and the spray orifice, outlets and liquid passageway are configured such that the rate of discharge onto the absorbent member exceeds the rate of spray discharge into the air, preferably by more than 2:1.

20 Claims, 5 Drawing Figures

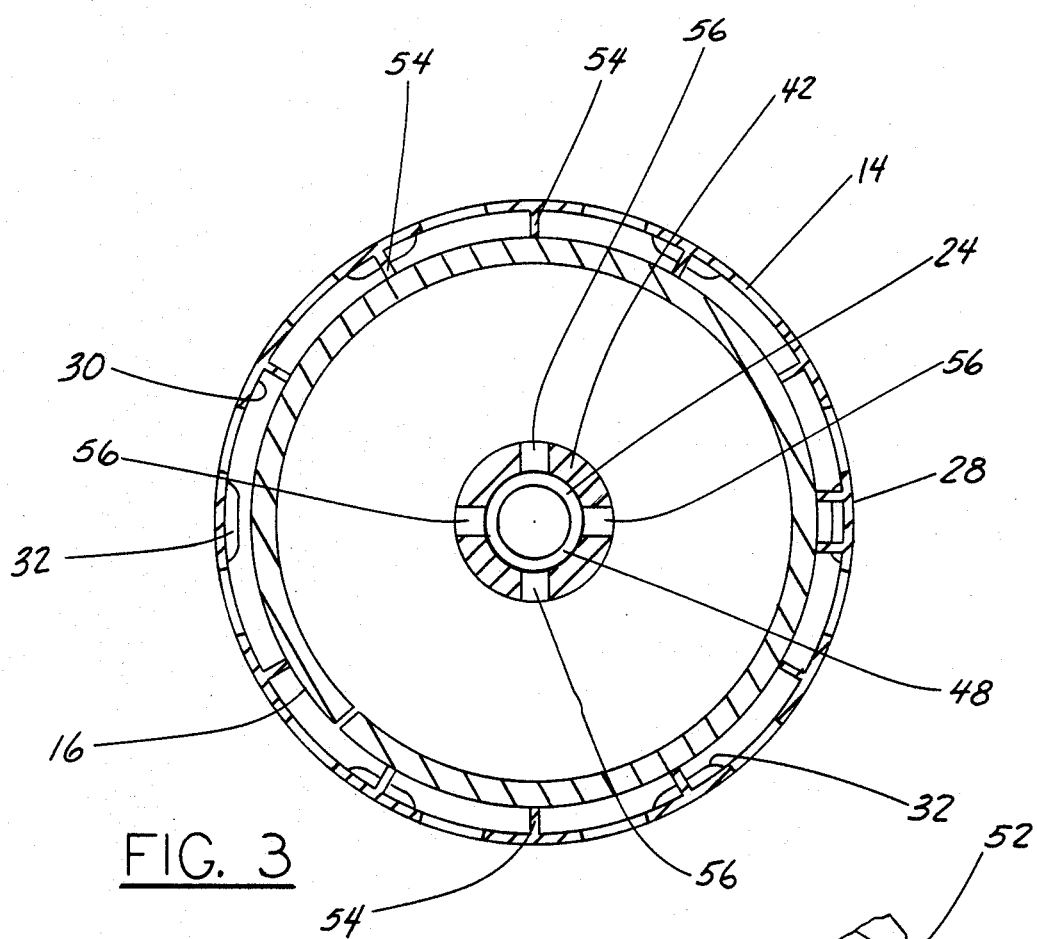
FIG. 3
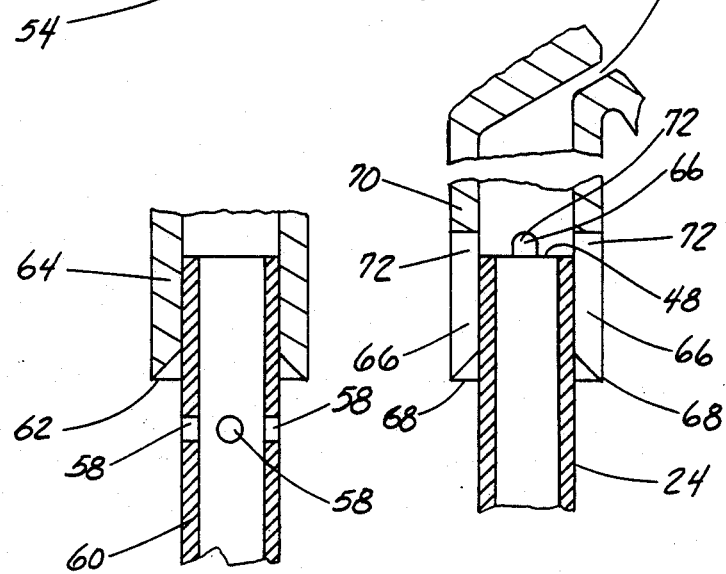
FIG. 4
FIG. 5

INSTANT/CONTINUOUS AIR-TREATMENT DEVICE

FIELD OF THE INVENTION

This invention is related generally to air treating and freshening and, more specifically, to pressurized dispensing devices for air-treating compositions. More specifically still, this invention is related to devices for dispensing air-treating liquid in two ways—quickly as sprays into the air, and continuously over extended periods as vapors.

BACKGROUND OF THE INVENTION

Concern about the quality of air has risen greatly in recent years. Developing means for the treatment of air for various purposes, including removing malodors, adding fragrances to the air, killing or repelling insects, and respiratory treatment, has become a major concern. This invention deals with devices for various air-treating purposes. For convenience, however, this invention and the problems which it addresses will be described primarily by reference to air fresheners.

A wide variety of devices have been developed for the dispensing of air-treating compositions. Two general approaches have been taken in dispensing air-freshening compositions: (1) spraying droplets of an air-treating liquid into the air, and (2) providing air-treating compositions on an absorbent element from which they continuously evaporate into the air over an extended period. The former method provides an instant burst of fragrance or other air-treating composition for immediate and intense air treatment. The latter method provides a continuous slow discharge of vapor to combat ambient odors.

Among the devices of the prior art used for air-treatment are those disclosed in the following U.S. Pat. Nos.:

2,520,468 (Landau)
2,987,261 (McCuiston et al.)
3,134,554 (Copley)
3,330,481 (Dearling)
3,940,024 (Russo)
3,972,473 (Harrison)
4,084,732 (Dearling)
4,235,373 (Clarke)
4,327,056 (Gaiser)
4,341,348 (Dearling)

Included in the prior art are devices intended for both instant and continuous treatment of the air. In some cases, devices of the prior art must be manipulated to achieve either an instant air treatment by discharge of a spray or recharge of a continuous air-treating element. The device described in U.S. Pat. No. 4,084,732, which is assigned to the assignee of the invention described and claimed herein, may be manipulated and adjusted for simultaneous spraying into the air and recharging of a continuous dispensing means.

The devices of the prior art have some very practical problems and disadvantages which make them ineffective and unacceptable for use in simultaneous instant-/continuous air treatment.

One problem relates to the dispensing habits of air-freshener users. Many people frequently use aerosol sprays to overcome intense malodors in bathrooms and other areas, and are very accustomed to the use of aerosols for that purpose. In sharp contrast, while many people have continuous air fresheners in their homes, they generally are unaware of the manner in which they operate.

For that reason and perhaps others, rechargeable air fresheners and so-called "dual use" products which require adjustment and manipulation for different kinds of use, or for simultaneous use, are not well understood. Referring specifically to dual use products, that is, products which can be used for spraying a mist into the atmosphere or for recharging a continuous air-freshener element, many people tend to ignore the recharging use and/or do not make the necessary adjustments and manipulations to make such use possible or, if the device allows, to make simultaneous use possible.

There is a need for a product which can readily be used for both instant air treatment by spraying a mist and for recharging of a continuous-action air-treating element.

A problem which is related, at least in that it is based in part on a lack of understanding of how continuous-action air fresheners work, is that such products are infrequently changed and remain in place long beyond their periods of effectiveness. There is a need for a continuous-action air-treating product which is effective throughout the period of its use. And, there is a need for a continuous-action air-treating product which has an easily-understandable indicator marking the end of its useful life.

Another significant and very practical problem with prior so-called dual use products is that their means for dispensing air-treating liquids, for recharging a continuous-action air-treating element and for spraying into the air, do not allow proper dispensing for both purposes. For example, if dispensing for recharging purposes is proper, then serious over-saturation of the air will typically occur. And, if dispensing into the air is proper, then recharging of the continuous air-treating element will be very inadequate.

This problem will be further described. In order to make a continuous-action air-freshener element function properly, it is necessary that the concentration of the perfume in the liquid to be dispensed onto the continuous-action absorbent element be quite high. However, based on normal user habits in spraying aerosol air-fresheners and on the need for a well-distributed mist, normal spraying of such a liquid composition would result in far too strong an odor in the air.

Therefore, there is clearly a need for an improved dual-use dispensing device for air-treating compositions which will allow both proper spraying of the air to overcome intense malodors and simultaneous proper recharging of a continuous-action air-treatment element. More specifically, there is a need for such a device which, while being used to spray the air in the normal fashion to overcome intense malodors, will properly and sufficiently recharge a continous-action element such that it will function properly for the necessary extended period.

SUMMARY OF THE INVENTION

This invention is a device for simultaneously spraying an air-treating composition into the air for instant air treatment and recharging an absorbent element for effective continuous air treatment. The invention overcomes the aforementioned problems and disadvantages of the prior art.

The device of this invention includes a pressurized vessel containing an air-treating liquid and having a protruding depressible valve stem, as is common for aerosol containers, an actuator-overcap with certain characteristics which is attached to the pressurized vessel and engages the valve stem, an absorbent member within the acuator-overcap, and means for simultaneously spraying the air-treating liquid into the air and discharging it onto the absorbent member for recharging it for continuous air-treatment purposes.

The actuator-overcap includes a vented wall, which is preferably cylindrical to conform to the shape of the preferred pressurized vessel, an actuator button, and a channel means which is secured to the actuator button. The channel means has a first end engaged with the valve stem and a second end terminating in a spray orifice which is directed outside the actuator-overcap and is used for spraying a mist into the air. The channel means and valve stem together form a passageway for fluid exiting the pressurized container.

The passageway has outlet means for directing the air-treating liquid onto the absorbent member when the device is being used for spraying the air. The spray orifice, the passage-way, and the outlet means are configured such that the rate of discharge through the outlet means exceeds the rate of discharge through the spray orifice. This is a factor which is important for proper operation of the device of this invention. The ratio of the rates of discharge through the outlet means and spray orifice is preferably at least 2:1 and optimally 2:1 to 5:1, although such ratio typically falls somewhat as the contents of the can are emptied.

The outlet means, through which air-treating liquid passes before hitting and being absorbed into the absorbent member, is preferably a plurality of laterally-directed outlets formed in the passageway. There are preferably three such laterally-directed outlets spaced around the axis which is defined by the valve stem, and most preferably there are four such outlets spaced at 90 degree intervals. The outlet means may be in the valve stem or in the channel means which is attached to it.

In the most preferred embodiments the actuator-overcap, including the vented wall, the actuator button, and the channel means, is an integrally-molded structure. The absorbent member is preferably an annulus, either continuous or broken, such as a cylindrical wall adjacent to the vented wall. In such position, the absorbent member will be impacted by air-treating liquid being dispensed from each of the laterally-directed outlets.

The vented wall of the actuator-overcap preferably has an inner surface with inwardly-extending ribs. The absorbent member is spaced from the vents in the wall by engagement with such ribs.

The relatively higher rate of discharge of air-treating liquid through the outlet means, as compared to the rate of discharge through the spray orifice, is important for proper functioning of the device of this invention. In order to properly recharge the absorbent member, a substantial amount of the active portion of the air-treating composition, such as perfume must be deposited on the absorbent member for proper functioning. By increasing the concentration of the perfume or other active in the liquid composition to be dispensed, and providing a slow rate of spray-discharge rate into the air relative to the rate of dispensing onto the absorbent member, the air can be properly treated by spraying of a mist at the same time as the absorbent member is properly charged or recharged for extended continuous air treatment.

The device of this invention has the additional advantage of requiring no manipulation or adjustment to achieve its dual-use function. Simple spraying in the normal manner for aerosol air fresheners will recharge the absorbent member, even if the user is unaware of what is happening.

Another important advantage of this invention is that it is a continous-action air-treating device which can easily remain at or near peak efficiency. And, it provides a use-up indicator which is easily understood—that is, spraying can no longer proceed because the contents of the container are depleted.

OBJECTS OF THE INVENTION

It is an object of this invention to provide an improved device for both instant and continuous dispensing of air-treating compositions which overcomes some of the disadvantages and problems of devices of the prior art.

Another object of this invention is to provide a dual-use air-treating device which requires little or no user learning for proper operation.

Another object of this invention is to provide a dual-use air-treating product which requires no manipulations or adjustments to prepare it for dispensing.

Another object of this invention is to provide a continuous-action air freshener which can easily be kept near peak efficiency throughout its life.

Another object of this invention is to provide a dual-use air-treating product which properly dispenses air-treating liquid into the air simultaneously with adequate dispensing of such liquid onto a continuous-action element.

Another object of this invention is to provide a continuous-action air freshener product which has an easily-understandable use-up indicator.

These and other objects will be apparent from the following additional descriptions and from the drawings, wherein:

BRIEF DESCRIPTION OF THE DRAWINGS

FIG. 3 is a sectional view taken along section 3—3 as indicated in FIG. 2, excluding the pressurized vessel except for illustration of the valve stem.

FIG. 4 is a fragmentary sectional view, taken along the valve stem axis, illustrating an alternative embodiment of this invention.

FIG. 5 is a a similar sectional view, taken along the valve stem axis, illustrating another alternative embodiment.

DETAILED DESCRIPTIONS OF PREFERRED EMBODIMENTS

Figure 1:
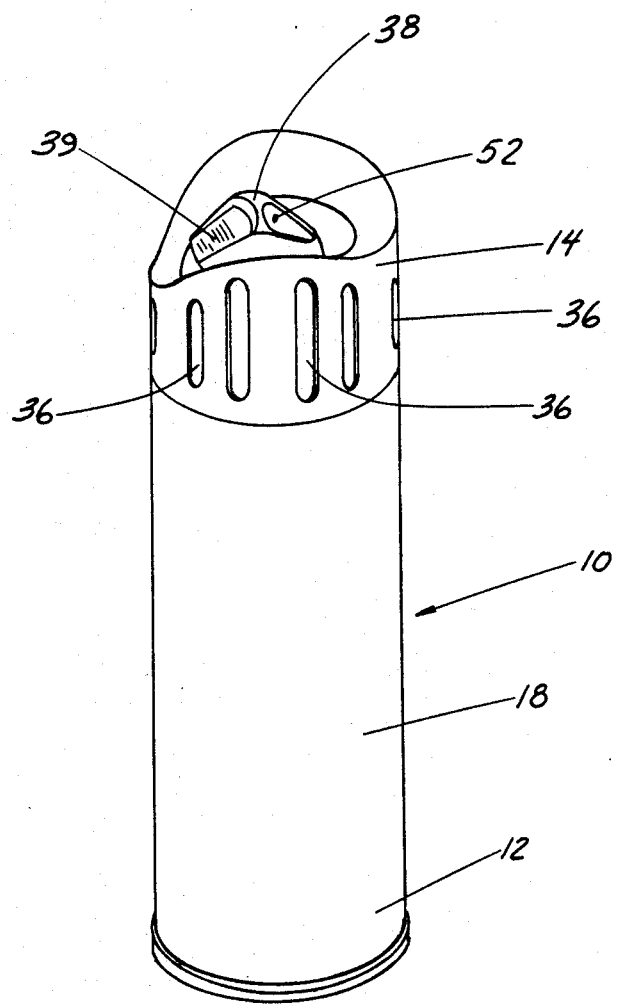
FIG. 1 is a perspective view of the preferred embodiment of this invention.
Figure 2:
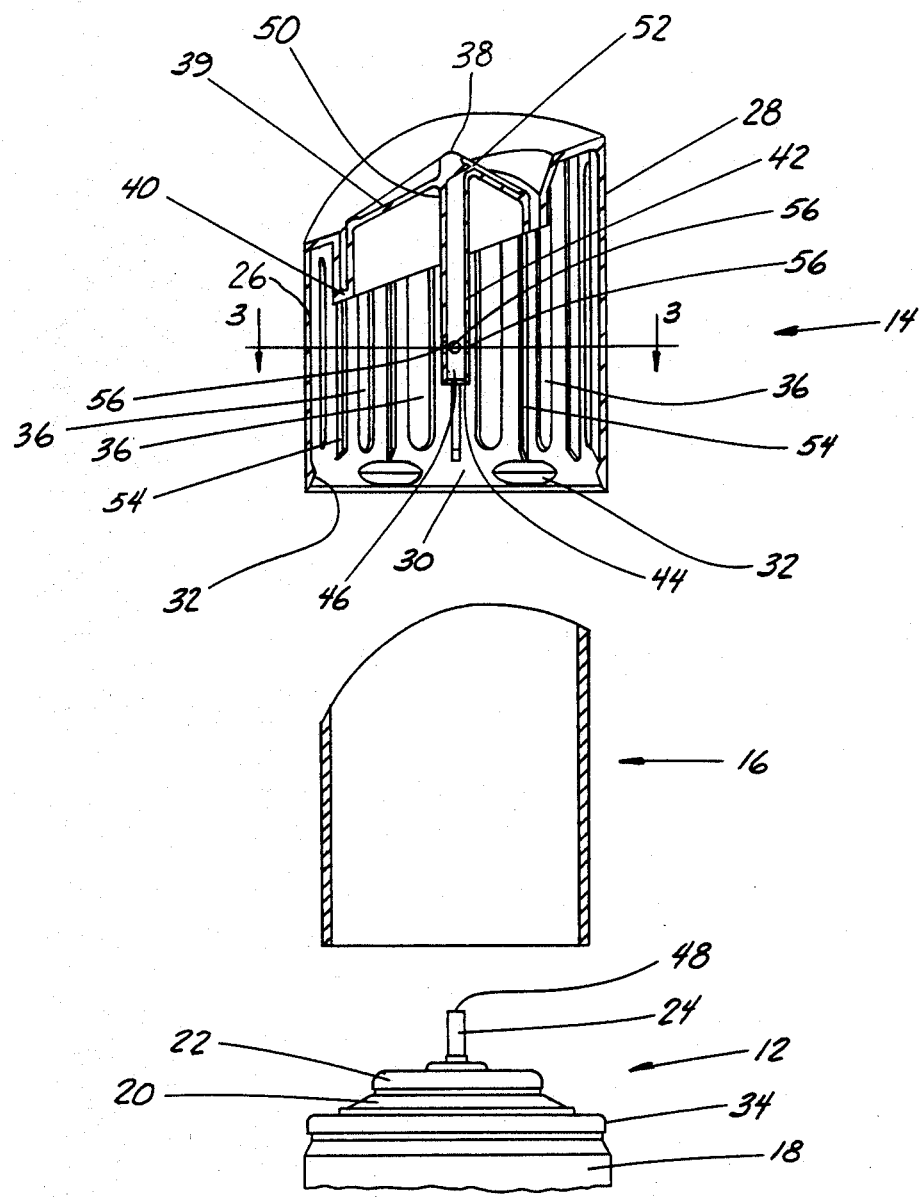
FIG. 2 is an enlarged fragmentary exploded sectional view of the device of FIG. 1, taken along its axis.

FIGS. 1-3 illustrate a preferred instant/continuous dispensing device 10 for dispensing air-treating vapors into the air. Dispenser 10 includes a pressurized vessel 12, an actuator-overcap 14, and an absorbent member 16.

Pressurized vessel 12, which is preferably a standard aerosol container, includes a cylindrical metal can 18, a dome top 20, which is doubleseamed onto can 18, and a valve cup 22 secured to dome top 20 and having a protruding valve stem 24. Valve stem 24 is along the axis defined by cylindrical can 18 and is depressible to actuate an aerosol valve (not shown) which is secured to valve cup 22. The aerosol valve has internal spring means which biases valve stem 24 to an upward non-dispensing position.

Actuator-overcap 14 is preferably an integrally-formed structure, formed by well-known molding procedures. Integrally-formed actuator-overcap 14 includes a cylindrical wall 26 having an outer surface 28, which is substantially flush with the cylindrical outer wall of metal can 18, and an inner surface 30. Extending radially inwardly from inner surface 30 are snap ridges 32 which snap over doubleseam 34 to attach actuator-overcap 14 to pressurized vessel 12.

Wall 26 of actuator-overcap 14 has several long vertical vents 36 through it which allow the free passage of ambient air into and out of actuator-overcap 14. Vents 36 are spaced around actuator-overcap 14 to facilitate free passage of air.

Actuator-overcap 14 also includes an actuator button 38, with a finger pad 39, a hinge 40 by which button 38 is joined to the remainder of actuator-overcap 14, and a channel member 42. Channel member 42 is secured to actuator button 38, both parts, along with hinge 40, having been formed integrally as parts of actuator-overcap 14.

Channel member 42 has an open lower end 44, sometimes referred to herein as a first end, which defines a socket 46 dimensioned to receive and hold the distal end 48 of valve stem 24 in fluid-tight fashion. Valve stem 24 and channel member 42 remain engaged, and together form a passageway for fluid exiting pressurized vessel 12. Channel member 42 also has an upper end 50, sometimes referred to herein as a second end, by which channel member 42 is secured to actuator button 38. Upper end 50 terminates in a spray orifice 52 which is directed outside actuator-overcap 14 for spraying of air-treating mist into the air. Channel member 42 is used not only for passage of liquid during dispensing, but provides the means by which the depression of actuator button 38 is transmitted to depressible valve stem 24.

Absorbent member 16 is preferably made of cellulosic or porous material capable of absorbing air-treating liquid, when such liquid is applied to it from pressurized vessel 12, and holding such liquid over a period of time for slow evaporation therefrom into air passing through vents 36. Absorbent member 16 is a rechargeable continuous air-treating device.

As used herein, the term "absorbent" is used herein in a broad sense. It refers to the ability of member 16 to receive and hold an air-treating liquid in any way for subsequent evaporation, including by absorption, adsorption or any physical-chemical process.

Absorbent member 16 is preferably in the form of a cylindrical annulus, as shown in FIGS. 2 and 3. Absorbent member 16 is within actuator-overcap 14 adjacent to inner surface 30 of actuator-overcap wall 26. Absorbent member 16 is positioned between the passageway comprising valve stem 24 and channel member 42. As will hereafter be seen, such positioning is important to facilitate the recharging of absorbent member 16 with air-treating liquid from pressurized vessel 12.

Actuator-overcap wall 26 has ribs 54 which extend radially inwardly from inner surface 30. Absorbent member 16 is engaged against ribs 54, and ribs 54 serve to space absorbent member 16 from vents 36. This facilitates full exposure of absorbent member 16 to ambient air flowing into actuator-overcap 14.

The passageway, which is made up of valve stem 24 and channel member 42, has outlet means for directing air-treating liquid onto absorbent member 16 during spraying of air-treating liquid into the air through orifice 52. The outlet means in the device of FIGS. 1–3 has four laterally-directed outlets 56 in channel member 42. Outlets 56 are spaced at 90 degree intervals around the axis defined by valve stem 24, and are at a common axial position, just above distal end 48 of valve stem 24.

Outlets 56, the passageway, and spray orifice 52 are configured such that the rate of discharge of liquid through the outlets 56 exceeds the rate of discharge through spray orfice 52. Such configuring includes the choice of the number of such outlets, in this case four, the choice of the sizes of such outlets and of spray orifice 52, the length of the fluid paths, and other factors. Other factors, such as the nature of the air-treating liquid, have a more limited effect on discharge rates.

Preferably the rate of discharge through the lateral outlet means is more than twice the rate of discharge through spray orifice 52. The ratio of discharge rates will typically drop over the life of the product. Preferred ratios of discharge rates are achieved with the embodiments shown. For example, the diameter of spray orifice 52, shown in FIG. 3 and in FIG. 5, is preferably on the order of 0.013 to 0.016 inch, while the diameter of outlets 56, shown in FIGS. 2 and 3, is on the order of 0.018 inch.

In preferred embodiments of this invention, the outlet means is formed by a plurality of laterally-directed outlets formed in the passageway, that is, either in valve stem 24 or in channel member 42 of actuator-overcap 14. It is preferred to have at least three such laterally-directed outlets, while having four such outlets as in the illustrated embodiments is most preferred. Such pluralities of laterally-directed outlets not only facilitate the required relative discharge rates of liquid going onto the absorbent member as opposed to liquid going directly into the air by spraying, but serve to apply the air-treating liquid onto the absorbent member at a plurality of locations. This provides a more even distribution of liquid into the absorbent member and facilitates absorption.

FIG. 4 shows an alternative embodiment. In FIG. 4, four outlets 58, three of which are illustrated, are formed by holes through valve stem 60. Outlets 58 are spaced about valve stem 60 at 90 degree intervals, at an axial position below the lower edge 62 of a channel member 64. In this embodiment, channel member 64 has no lateral outlets, but is used to carry liquid upwardly to the spray orifice.

FIG. 5 shows another alternative embodiment. In FIG. 5, four parallel slots 66 extend from the lower edge 68 of channel member 70 upwardly to positions just above distal edge 48 of valve stem 24. The portions of slots 66 which extend beyond distal edge 48 form outlets 72 through which air-treating liquid from pressurized vessel 12 is discharged onto absorbent member 16. Slots 66 and outlets 72 are spaced at 90 degree intervals around channel member 70.

Outlets 58 and 72 in embodiments illustrated in FIGS. 4 and 5, respectively, are sized and otherwise configured to achieve the preferred relative discharge rates into the absorbent members and into the air.

When dispenser 10 is being used for instant treatment of the air, absorbent member 16 is automatically being charged or recharged with air-treating liquid to prepare it for continuous treatment of the air by evaporation of such liquid into the air over an extended period of time. No separate preparatory step or other action is necessary to achieve such charging or recharging. Good continuous air-treating action is achieved by the user without any separate mental step on his or her part.

By virtue of this invention, a continuous action air freshener can remain at peak or near peak vapor-dispensing efficiency throughout much of the life of the product. And it can do so without an intentional recharging program.

Actuator-overcap 14 may be made using any of several common plastics used for making overcaps and the like. Examples of acceptable materials include polypropylene and polyethylene. Acceptable materials would be well known to those skilled in the art who are familiar with this invention.

Acceptable aerosol compositions likewise would be familiar to those skilled in the art who are familiar with this invention. Acceptable compositions can be solution systems or emulsion systems, with well-known ingredients including a high-level of actives, sucn as perfumes in air-freshening compositions. Of course, such compositions will include propellents.

In typical aerosol air-freshener compositions, perfume is included in amounts on the order of about 0.2 to 0.6% by weight of the composition, although perfume amounts may vary substantially. The most preferred compositions for use with the dispensing device of this invention include perfume in amounts on the order of 1 to 3%.

While the principles of this invention have been described in connection with specific embodiments, it should be understood clearly that these descriptions are made only by way of example and are not intended to limit the scope of the invention.

What is claimed:

1. A device for both instant and continuous dispensing of air-treating composition comprising:
   a pressurized vessel containing air-treating liquid and having a protruding depressible valve stem;
   an actuator-overcap attached to the vessel and including a vented wall, an actuator button, and channel means secured to the button and having a first end engaged with the stem and a second end terminating in a spray orifice directed outside the actuator-overcap, said channel means and stem forming a passageway for fluid exiting the vessel;
   an absorbent member within the actuator-overcap between the passageway and the vented wall; and
   outlet means in said passageway for directing the liquid onto the absorbent member during spraying through the spray orifice, the outlet means, passageway and spray orifice being configured such that the rate of discharge through the outlet means exceeds the rate of discharge through the spray orifice,
   wherein the outlet means, passageway and spray orifice are configured such that the ratio of the rate of discharge through the outlet means to the rate of discharge through the spray orifice is at least 2:1.

2. The device of claim 1 wherein the outlet means, passageway and spray orifice are configured such that the ratio of the rate of discharge through the outlet means to the rate of discharge through the spray orifice is from 2:1 to 5:1.

3. The device of claim 2 wherein the outlet means comprises a plurality of laterally-directed outlets formed in the passageway.

4. The device of claim 3 having at least three of said outlets spaced around the axis formed by the valve stem.

5. The device of claim 4 having four outlets spaced at 90 degree intervals.

6. The device of claim 1 wherein the outlet means is formed in the valve stem.

7. The device of claim 6 wherein the outlet means comprises a plurality of laterally-directed outlets.

8. The device of claim 7 having at least three of said outlets spaced around the axis formed by the valve stem.

9. The device of claim 8 having four outlets spaced at 90 degree intervals.

10. The device of claim 1 wherein the outlet means is formed in the channel means.

11. The device of claim 10 wherein the outlet means comprises a plurality of laterally-directed outlets.

12. The device of claim 11 having at least three of said outlets spaced around the axis formed by the valve stem.

13. The device of claim 12 having four outlets spaced at 90 degree intervals.

14. The device of claim 1 wherein the actuator-overcap, including the vented wall, the actuator button, and the channel means is an integrally-molded structure.

15. The device of claim 14 wherein the absorbent member is an annulus adjacent to the vented wall.

16. The device of claim 15 wherein the vented wall has an inner surface having inwardly-extending ribs, said absorbent member being spaced from the vents in the wall by engagement with said ribs.

17. The device of claim 16 wherein the outlet means comprises a plurality of laterally-directed outlets formed in the passageway.

18. The device of claim 17 having at least three of said outlets spaced around the axis formed by the valve stem.

19. The device of claim 18 wherein the outlets are formed in the valve stem.

20. The device of claim 18 wherein the outlets are formed in the channel means.

* * * * *